United States Patent
Javitt

(10) Patent No.: US 6,355,681 B2
(45) Date of Patent: *Mar. 12, 2002

(54) GLYCINE SUBSTITUTES AND PRECURSORS FOR TREATING A PSYCHOSIS

(75) Inventor: Daniel C. Javitt, Riverdale, NY (US)

(73) Assignee: Glytech, Inc., Riverdale, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/320,446

(22) Filed: May 27, 1999

Related U.S. Application Data

(60) Continuation-in-part of application No. 09/212,273, filed on Dec. 16, 1998, now Pat. No. 6,162,827, which is a division of application No. 08/759,714, filed on Dec. 6, 1996, now Pat. No. 5,854,286.
(60) Provisional application No. 60/008,361, filed on Dec. 7, 1995.

(51) Int. Cl.$^7$ .......................... A01N 37/12; A61K 31/70
(52) U.S. Cl. .......................... 514/561; 514/42; 514/45; 514/49; 930/21
(58) Field of Search .......................... 514/531, 561, 514/551, 578, 563, 762, 663, 554, 474, 458, 49, 45, 42

(56) References Cited

U.S. PATENT DOCUMENTS

| | | | |
|---|---|---|---|
| 4,904,681 A | | 2/1990 | Cordi et al. |
| 5,068,412 A | | 11/1991 | Ohfune et al. |
| 5,086,072 A | | 2/1992 | Trullas et al. |
| 5,179,085 A | | 1/1993 | Bigge et al. |
| 5,187,171 A | | 2/1993 | Cordi et al. |
| 5,260,324 A | | 11/1993 | Cordi et al. |
| 5,428,069 A | | 6/1995 | Skolnick et al. |
| 5,656,608 A | * | 8/1997 | Schneider et al. ............. 514/42 |
| 5,756,348 A | | 5/1998 | Smith et al. |
| 5,837,730 A | * | 11/1998 | Javitt ........................ 514/551 |
| 5,854,286 A | * | 12/1998 | Javitt et al. ................ 514/561 |

FOREIGN PATENT DOCUMENTS

| | | | | |
|---|---|---|---|---|
| WO | 97/20553 | * | 6/1997 | ......... A61K/31/195 |

OTHER PUBLICATIONS

D'Souza et al., "Glycine Site Agonists of the NMDA Receptor: A Review," CNS Drug Reviews, vol. 1, No. 2, pp. 227–260, 1995.*
D'Souza et al., "Intravenous Glycine and Oral D–Cycloserine Effects on CSF Amino Acids, Plasma Hormones and Behavior in Healthy Humans: Implications for Schizophrenia," Schiz. Res., 15:147, 1995.*
Davis KL, Kahn RS, Ko G, Davidson M (1991): Dopamine in schizophrenia: a review and reconceptualization. Am J Psychiatry 148:1474–1486.
Debler EA, Lajtha A (1987): High–affinity transport of n–aminobutyric acid, glycine, taurine, L–aspartic acid, and L–glutamatic acid in synaptosomal (P2) tissue: a kinetic and substrate specificity analysis. J Neurochem 48:1851–6.
D'Souza DC, Charney D, Krystal J (1995): Glycine site agonists of the NMDA receptor: a review. CNS Drug Revs 1:227–260.
Hashimoto A, Oka T (1997): Free D–aspartate and D–serine in the mammalian brain and periphery. Prog. Neurobiol 52:325–353.
Heresco–Levy U, Javitt DC, Irmilov M, Mordel C, Horowitz A, Kelly D (1996): Double–blind, placebo–controlled, crossover trial of glycine adjuvant therapy for treatment–resistant schizophrenia. Br J Psychiatry 169:610–617.
Javitt DC, Sershen H, Hashim A, Lajtha A (1997): Reversal of phencyclidine–induced hyperactivity by glycine and the glycine uptake antagonist glycyldodecylamide. Neuropsychopharmacol 17:202–204.
Javitt DC, Frusciante MJ. (1997): Glycyldodecylamide, a phencyclidine behavioral antagonist, blocks cortical glycine uptake: Implications for schizophrenia and substance abuse. Psychopharmacol. 129: 96–98.
Javitt DC, Zylberman I, Zukin SR, Heresco–Levy U, Lindenmayer JP (1994): Amelioration of negative symptoms in schizophrenia by glycine. Am J Psychiatry 151:1234–1236.
Javitt DC, Zukin SR (1991): Recent advances in the phencyclidine model of schizophrenia. Am J Psychiatry 148:1301–8.
Javitt DC, Zukin SR (1989): Interaction of [$^3$H]MK–801 with multiple states of the N–methyl–D–aspartate receptor complex of rat brain. Proc. Nat. Acad. Sci. USA 86:740–744.
Javitt DC (1987): Negative schizophrenic symptomatology and the phencyclidine (PCP) model of schizophrenia. Hill J Psychiat 9:12–35.
Kleckner NW, Dingledine R (1988): Requirement for glycine in the activation of NMDA–receptors expressed in Xenopus ooctyes. Science 241:835–837.
Leiderman E, Zylberman I, Javitt DC, Zukin SR, Cooper TB. Effect of high–dose oral glycine on serum levels and negative symptoms in schizophrenia. Biol. Psychiatry, in press.
Liu QR, Lopez–Corcuera B, Mandiyan S, Nelson H, Nelson N (1993): Cloning and expression of spinal cord– and brain–specific glycine transporter with novel structural features. J Biol Chem 268:22802–8.

(List continued on next page.)

Primary Examiner—Padmashri Ponnaluri
(74) Attorney, Agent, or Firm—Sughrue Mion, PLLC

(57) ABSTRACT

Process for treating psychosis such as schizophrenia using a glycine substitute or a precursor thereof to potentiate NMDA receptormediated neurotransmission.

4 Claims, 5 Drawing Sheets

OTHER PUBLICATIONS

Matsui T, Sekiguchi M, Hashimoto A, Tomita V, Nishikawa T, Wada K (1995) Functional comparison of D–serine and glycine in rodents: the effect on cloned NMDA receptors and the extracellular concentration. J Neurochem. 65:454–458.

McBain CJ, Kleckner NW, Wyrick S, Dingledine R (1989): Structural requirements for the glycine coagonist site of N–methyl–D–aspartate receptors expressed in *Xenopus oocytes*. Mol Pharmacol 36:556–565.

Reynold IJ, Murphy SN, Miller RJ (1987): 3H–labeled MK–801 binding to the excitatory amino acid receptor complex from rat brain is enhanced by glycine. Proc. Natl. Acad. Sci. USA 84:7744–7748.

Schell MJ, Molliver ME, Snyder SH (1995). D–serine, an endogenous synaptic modulator: localization to astrocytes and glutamate–stimulated release. Proc. Natl. Acad. Sci. USA 92:3948–3952.

Smith KE, Borden LA, Hartig PR, Branchek T, Weinshank RL (1992): Cloning and expression of a glycine transporter reveal colocalization with NMDA receptors. Neuron 8:927–35.

Supplisson S, Bergman C (1997): Control of NMDA receptor activation by a glycine transporter co–expressed in *Xenopus oocytes*. J Neurosci 17:4580–90.

Tanii Y, Nishikawa T, Hashimoto A, Takahashi K (1991): Stereoselective inhibition by D– and L–alanine of phencyclidine–induced locomotor stimulation in the rat. Brain Res 563:281–284.

Tanii Y, Hishikawa T, Hashimoto A, Takahashi K (1994): Stereoselective antagonism by enantiomers of alanine an d–serine of phencyclidine–induced hyperactivity, stereotypy and ataxia. J. Pharmacol. Exp. Ther. 269:1040–1048.

Tsai G, Yang P, Chung L–C, Lange N, Coyle JT (1998): D–serine in the treatment of schizophrenia. Biol. Psychiatry 44:1081–1089.

Wood PL (1995): The co–agonist concept: is the NMDA–associated glycine receptor saturated in vivo? Life Sci 57:301–10.

Wong EH, Knight AR, Ransom R (1987) Glycine modulated [3H]MK–801 binding to the NMDA receptor in rat brain. Eur J Pharmacol 142:487–8.

Zafra F, Aragon C, Olivares L, Danbolt NC, Gimenez C, Storm–Mathisen J (1995): Glycine transporters are differentially expressed among CNS cells. J Neurosci 15:3952–69.

Michael J. Schell, et al. "D–Serine as a Neuromodulator: Regional and Developmental Locaizations in Rat Brain Glia Resemble NMDA Receptors" The Journal of Neuroscience, Mar. 1, 1998, 17(5): 1604–1615.

* cited by examiner

FIGURE 1. Negative symptom levels derived from the Positive and Negative Syndrome Scale (PANSS) for subjects during treatment with glycine and D-cycloserine. Circles represent individuals treated with conventional antipsychotics (open circles) or clozapine (closed circles). Bars represent group means.
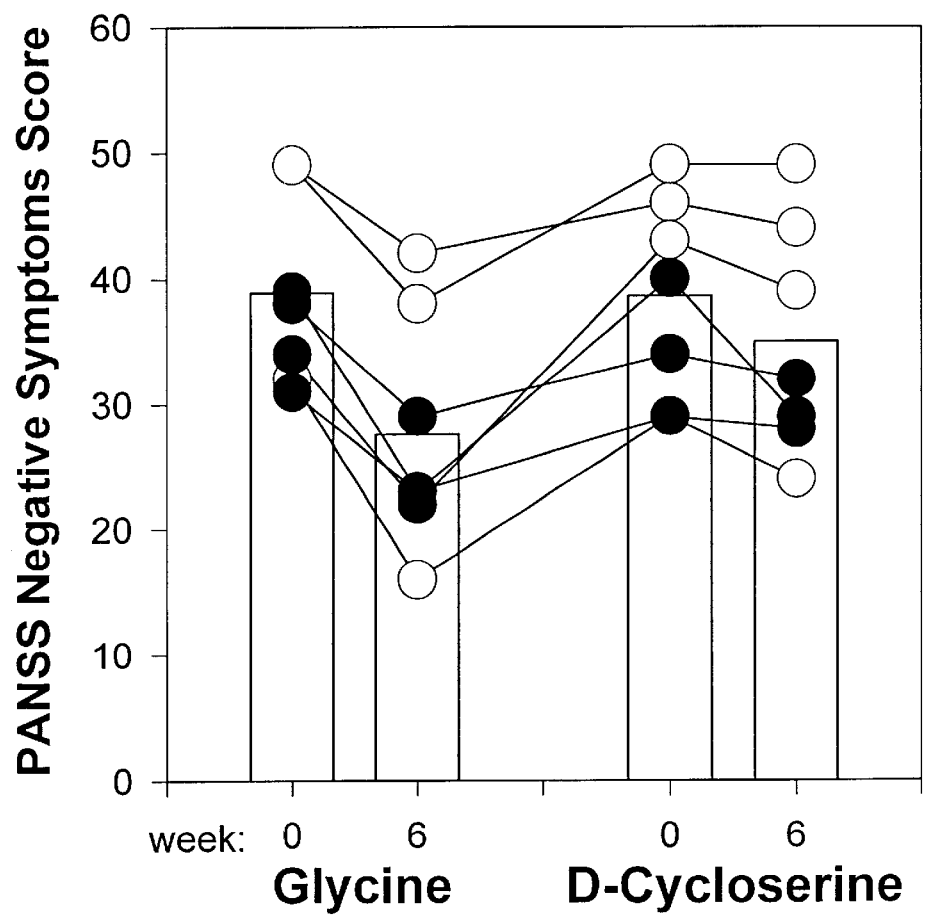

Figure 2 - Effects of glycyldodecylamide (GDA) on locomotor hyperactivity induced by phencyclidine (PCP) or amphetamine. Bars are mean ± s.e.m.  *** p<.001 vs. ctl
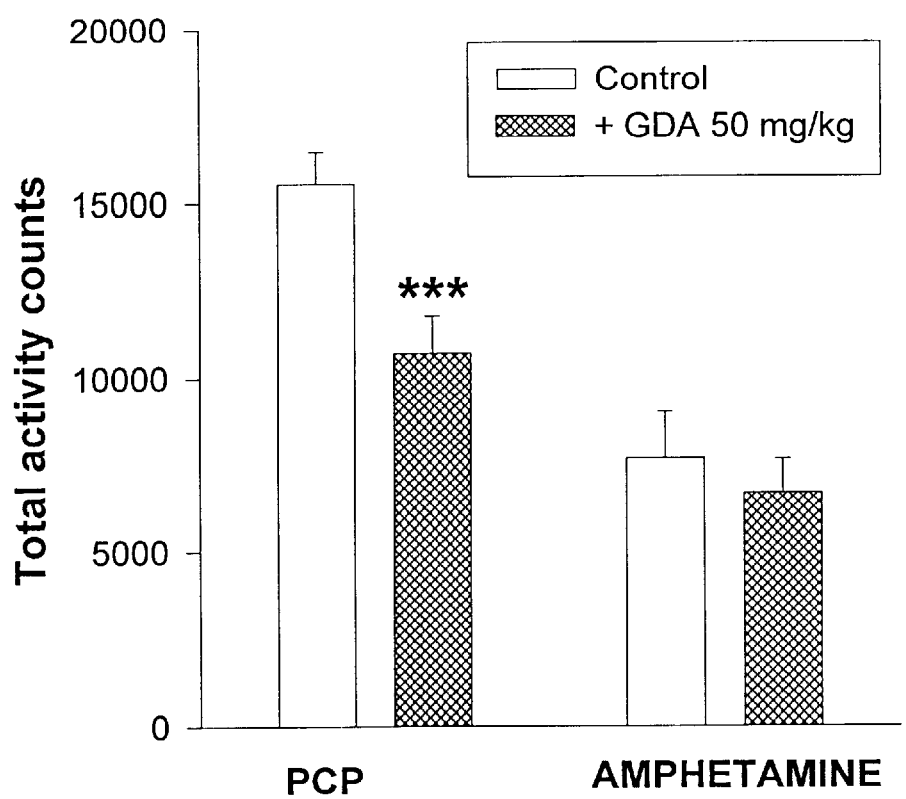

Figure 3 - Effect of a series of glycineamide derivatives on locomotor hyperactivity induced by PCP. All agents were given at a dose of 100 mg/kg. Bars are mean ± s.e.m. * p<.05 vs. ctl. ** p<.01 vs. ctl
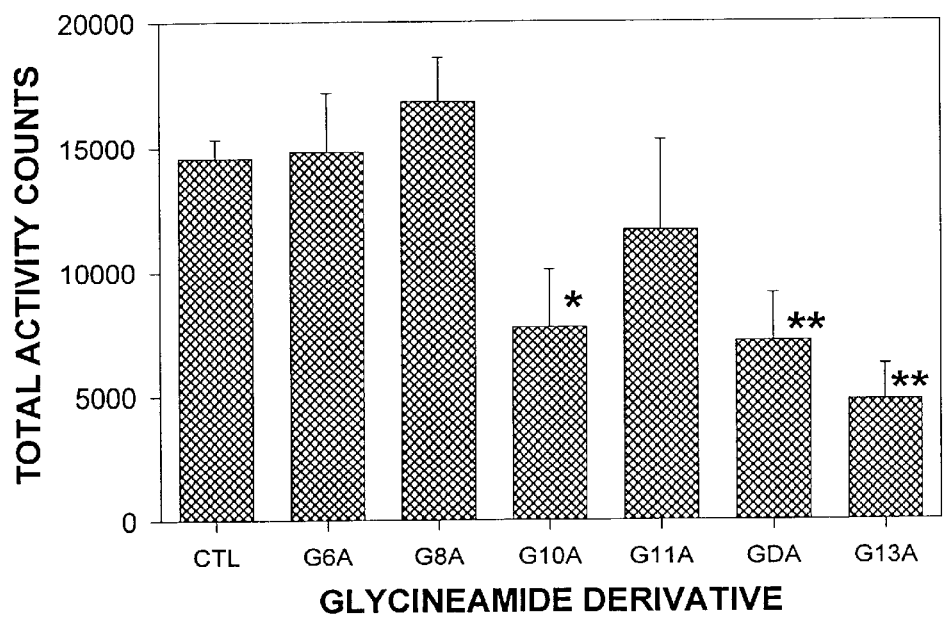

Figure 4 - Inhibition of [$^3$H]glycine transport (glycine uptake) in P2 synaptosomal fractions by indicated concentrations of glycineamide derivatives.
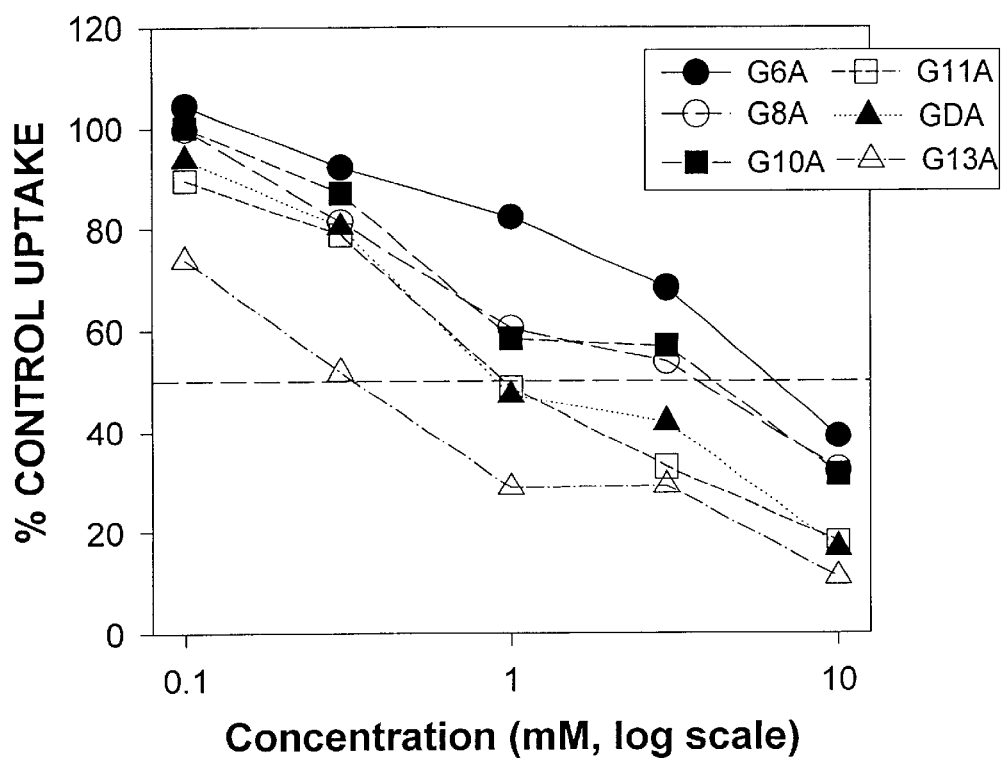

Figure 5 - Scatter plot showing the relationship between potency in reducing PCP-induced hyperactivity in vivo and potency in inhibiting synaptosomal glycine uptake in vitro. For in vivo experiments, agents were tested at a dose of 100 mg/kg. For uptake experiments, agents were tested at a dose of 100 μg/ml.
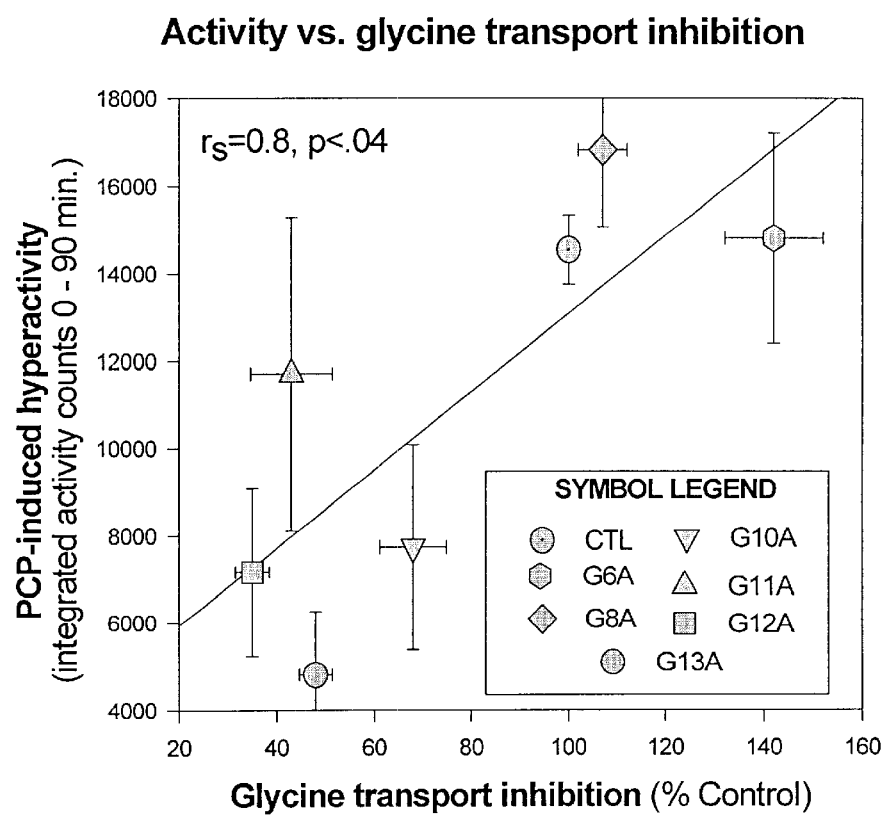

GLYCINE SUBSTITUTES AND PRECURSORS FOR TREATING A PSYCHOSIS

RELATED APPLICATIONS

This application is a continuation-in-part application of prior application 09/212,273 filed Dec. 16, 1998, now U.S. Pat. No. 6,162,827, in turn a divisional application of 08/759,714 filed Dec. 6, 1996 (now U.S. Pat. No. 5,854,286). Priority is claimed from Provisional application Ser. No. 60/008,361 filed Dec. 7, 1995. The subject matters of the prior applications are incorporated in their entirety herein by reference thereto.

BACKGROUND

Traditional models of schizophrenia have focused on dopaminergic systems. More recent models, however, derive from the phencyclidine (PCP, "angel dust") model of schizophrenia (Javitt, 1987; Javitt and Zukin, 1991) and postulate that schizophrenia is associated with dysfunction or dysregulation of neurotransmission mediated at brain N-methyl-D-aspartate (NMDA)-type glutamate receptors. The PCP/NMDA model of schizophrenia raised the possibility that agents which augment NMDA receptor-mediated neurotransmission might be therapeutically beneficial in schizophrenia. The primary neurotransmitter acting at NMDA receptors is glutamate. However, NMDA receptor activity is also modulated by the amino acid glycine which binds to a selective modulatory site that is an integral component of the NMDA receptor complex. U.S. Pat. No. 5,854,286 discloses the use of orally administered glycine, in dietary quantities, for the treatment of schizophrenia.

Glycine is considered a full agonist at the NMDA-associated glycine binding site (McBain et al., 1989). The clinical findings with glycine detailed in the prior patents U.S. Pat. No. 5,854,286 and U.S. Pat. No. 5,837,730 applications therefore, provided the first evidence that glycine-site full agonists are effective in the treatment of schizophrenia. This concept has also recently been supported by a study utilizing D-serine (Tsai et al., 1998), an alternative glycine site full agonist (McBain et al., 1989; Javitt et al., 1989; Kleckner and Dingledine, 1988; Wong et al., 1987; Reynolds et al., 1987), consistent with the ability of this compound to induce glycine-like behavioral effects in rodents (Tanii et al., 1994, 1991) and to penetrate into CNS following peripheral administration (Hashimoto and Oka, 1997). D-Serine, like glycine, is present in brain in high concentration and may serve as an endogenous ligand for the glycine binding site of the NMDA receptor complex (Schell et al., 1995). The use of D-serine, along with use of other agents that might substitute for glycine at the glycine site of the NMDA receptor complex, was disclosed in the above noted U.S. patents and in Provisional application 60/008361 filed Dec. 1, 1995.

Although the findings with glycine and D-serine support the use of full glycine-site agonists, others have proposed that partial agonists at the glycine site, such as the drug D-cycloserine, should be more effective than full agonists in the treatment of schizophrenia (Cordi, patent No. 5,187,171). Partial agonists bind to the same site as full agonists (i.e., glycine recognition site of the NMDA receptor complex), but potentiate channel opening only to a much smaller percent (typically 40–70% of the activation seen with full agonists, McBain et al., 1989). Clinical studies with D-cycloserine have provided support for the concept that partial glycine-site antagonists may be effective in the treatment of schizophrenia (reviewed in D'Souza et al., 1995), and, the degree of improvement seen in studies of D-cycloserine (reviewed in D'Souza et al., 1995) has been comparable in some circumstances to the degree of improvement observed following studies with glycine (Heresco-Levy et al., 1996; Leiderman et al., 1996 and reviewed in D'Souza et al., 1995) or D-serine (Tsai et al., 1998). No study has yet compared the effectiveness of glycine treatment to that of D-cycloserine treatment.

A second potential approach to augmentation of NMDA receptor-mediated neurotransmission is the administration of agents that inhibit glycine transporters in brain, thereby preventing glycine removal from active sites within CNS. It has been known for many years that the brain contains active transport systems for glycine that may regulate brain levels (Debler and Lajtha, 1987; D'Souza, 1995). More recent studies demonstrated that glycine transporters are differentially expressed in different brain region (Liu et al, 1993; Zafra et al., 1995) and may be co-localized with NMDA receptors (Smith et al., 1992). However, it has also been known for many years that extracellular glycine levels are beyond the level needed to saturate the NMDA-associated glycine binding site, making it unclear whether glycine transporters are, in fact, able to maintain subsaturating glycine levels in the immediate vicinity of NMDA receptors. This is a crucial issue in that, if glycine levels were already at or above saturating levels, additional glycine would not, on theoretical grounds, be able to stimulate NMDA functioning (Wood, 1995).

U.S. Pat. No. 5,837,730, to the current inventor provided the first evidence that an identified glycine transport inhibitor, glycyldodecylamide (GDA), was able to exert glycine-like, anti-PCP behavioral effects in rodents, and thus the first evidence that glycine transport inhibitors should exert glycine-like amelioration of negative and cognitive symptoms in schizophrenia. In U.S. Pat. No. 5,837,730, data were presented from a series of three compounds demonstrating appropriate rank order of potency of these compounds in producing glycine-like behavioral effects in rodents.

BRIEF DESCRIPTION OF THE DRAWING

FIG. 1 plots negative symptom levels derived from the Positive and Negative Syndrome Scale (PANSS) for subjects during treatment with glycine and D-cycloserine. Circles represent individuals treated with conventional antipsychotics (open circles) or clozapine (closed circles). Bars represent group means.

FIG. 2 depicts effects of glycyldodecylamide (GDA) on locomotor hyperactivity induced by phencyclidine (PCP) or amphetamine. Bars are mean±s.e.m. ***$p<0.001$ vs. ctl FIG. 3 depicts effect of a series of glycineamide derivatives on locomotor hyperactivity induced by PCP. All agents were given at a does of 100 mg/kg. Bars are mean±s.e.m. *$p<0.05$ vs. ctl. **$p<0.01$ vs. ctl FIG. 4 depicts inhibition of [$^3$H]glycine transport (glycine uptake) in P2 synaptosomal fractions by indicated concentrations of glycineamide derivatives.

FIG. 5 is a scatter plot showing the relationship between potency in reducing PCP-induced hyperactivity in vivo and potency in inhibiting synaptosomal glycine uptake in vitro. For in vivo experiments, agents were tested at a dose of 100 mg/kg. For uptake experiments, agents were tested at a dose of 100 μg/ml.

SUMMARY OF THE INVENTION

It is therefore unknown whether full agonists at the glycine-site as a class are more or less effective than partial agonists, and thus, it is unknown whether glycine site full-agonists as a class would be more beneficial in the treatment of persistent negative symptoms of schizophrenia. The present application provides the first direct comparison of the effectiveness of full and partial glycine agonists in the treatment of schizophrenia (Study 1, below). It demonstrates that the full agonist, glycine, produces significantly greater symptomatic improvement than the partial agonist D-cycloserine among subjects who received both treatments in placebo controlled, double blind trials. This study, therefore, provides the first evidence that substitutes for glycine at the glycine site (which are full glycine agonists) as a class, are more effective than partial agonists. Other glycine substitutes at the glycine site include D-isomers of serine and alanine (McBain et al., 1989) and optimized derivatives thereof. Other agents such as glycineamide, threonine or glycine polypetides or glycine prodrugs are metabolized in brain to glycine, and should serve as active precursors of glycine and/or serine in the treatment of schizophrenia. Other amino acids, prodrugs or polypeptides which serve as precursors for other full glycine agonists in CNS can be employed. This may be accomplished by microencapsulation of glycine, for example using liposomes, for delivery to CNS, or by construction of polyglycine or polyserine vectors incorporating a CNS targeted moiety chosen to encourage penetration into CNS.

In another embodiment, the present inventor can now demonstrate that the ability of glycine transport inhibitors to reverse PCP-induced behavioral effects correlates significantly with their ability to inhibit glycine transport in vitro, supporting the discovery that such agents exert their glycine-like behavioral effects by blocking brain glycine transport. A number of glycylakylamides are tested herein (Study 2).

DETAILED DESCRIPTION

Study 1—Relative effectiveness of a glycine binding site full agonist (glycine) and partial agonist (D-cycloserine) in the treatment of schizophrenia.
Rationale Endogenous dysfunction or dysregulation of neurotransmission mediated at NMDA-type glutamate receptors may contribute significantly to the pathophysiology of negative and cognitive symptoms of schizophrenia. NMDA receptor activation is regulated not only by glutamate but also by glycine, which mediates its action at a strychnine-insensitive binding site associated with the NMDA receptor complex. Glycinergic agents, therefore, may be therapeutically beneficial in schizophrenia.

Two potential agents have been suggested as potential agents for stimulation of NMDA receptor-mediated neurotransmission in schizophrenia: glycine and D-cycloserine (reviewed in D'Souza et al., 1995). Glycine is a naturally occurring amino acid and a normal dietary constituent. Glycine acts as a full agonist at the NMDA-associated glycine binding site, but must be given at large (>30 g/day) doses because of its poor permeability across the blood brain barrier. D-Cycloserine is an anti-tubercular drug that also functions as a partial agonist at the NMDA-associated glycine site. D-Cycloserine readily crosses the blood-brain barrier. However, D-cycloserine is only 40% as effective as glycine in potentiating NMDA receptor-mediated neurotransmission. Thus, at high doses, D-cycloserine may act as a functional glycine antagonist. Both glycine (the present inventor) and D-cycloserine (D'Souza et al., 1995) are reported to significantly ameliorate neuroleptic-resistant negative symptoms in schizophrenia. The relative effectiveness of these two agents, however, has not been compared.

METHODS

Seven subjects were identified who participated in each of two separate studies investigating effects of NMDA augmenting agents in schizophrenia. The first investigated effects of 0.8 g/kg/day (approx. 60 g/day) glycine. The second study investigated effects of 50 mg/day D-cycloserine. Separate informed consent was obtained for each study. Subjects met DSM-IV criteria for schizophrenia and were free of other Axis I diagnoses (including substance abuse) or concurrent medical illness. All met criteria for neuroleptic-resistance, and manifested moderate-to-severe symptoms despite continuous neuroleptic treatment for at least 3 months. Mean age of the patients upon study entry was 39.9±15.7 yrs (Table 1). Patients had been ill, on average, for 20.1±13.4 yrs. at the time of study entry. Their duration of most recent hospitalization was 8.5±7.4 yrs.

Both studies were conducted using a double blind, placebo-controlled crossover design. Total study length was 16 weeks. Patients underwent an initial 2 week stabilization period, following by 6 weeks of treatment with either active medication or placebo. They then underwent a 2-week washout followed by 6 weeks of crossover treatment. Antipsychotic dose was held constant throughout each trial. Symptom ratings were performed using the Positive and Negative Syndrome Scale (PANSS). One patient discontinued during week 4 of D-cycloserine treatment due to symptom exacerbation, and was not available for the placebo treatment arm.

Statistical analyses (two-tailed) were accomplished using the SPSS computer program. Pre-vs. post-treatment comparisons were performed using paired t-tests. Treatment vs. placebo effects were evaluated using repeated measures ANOVA. Values in text represent mean±standard deviation.

RESULTS AND DISCUSSION

At entry into the glycine treatment study, the baseline negative symptom score for the 7 subjects was 39.0±6.6. During glycine treatment, subjects experienced an 11.3±3.6 point reduction in negative symptoms ($t=8.21$, $df=6$, $p<0.0001$), corresponding to a mean 28.5% reduction in symptoms (FIG. 1). In contrast, negative symptoms increased by 0.1±1.7 points during treatment with placebo. The treatment by time interaction was highly significant ($F[1,6]=83.5$, $p<0.001$). Positive symptoms did not change significantly from beginning (25.7±7.0 points) to end (22.0±4.0 points) of glycine treatment. However, a significant, 13.0±7.7 point change in general psychopathology from 56.0±19.4 to 43.0±13.8 points was observed ($t=4.44$, $df=6$, $p<0.005$). This reduction corresponded to a 23.2% decrease in symptoms.

Following completion of the double blind glycine treatment study, subjects included in this report were treated with antipsychotics alone for a mean duration of 15.6±5.9 mo. (range: 6–23 mo.) before being entered into the D-cycloserine study. The mean negative symptom score for these subjects upon entry into the D-cycloserine study, 39.0±7.8, was highly similar to the score that had been observed prior to glycine treatment. Medications and doses used during the D-cycloserine trial were similar to those used during the prior glycine trial (Table 1).

During D-cylloserine treatment, subjects experienced a significant, 3.6±3.7 point reduction in negative symptoms ($t=2.56$, $p<0.05$), corresponding to a mean 9.2% decrease in symptoms. In contrast, the degree of negative symptom reduction during placebo treatment for these subjects, 1.0±3.1 points, was not significant. However, the treatment by time interaction was not significant (F[1,5]=1.87, p=0.23). Positive symptoms and general psychopathology scores did not change significantly during treatment with either D-cycloserine or placebo.

In order to assess relative effectiveness of glycine and D-cycloserine for treatment of negative symptoms in these subjects, negative symptom change scores were compared across the two trials. The degree of reduction in negative symptoms observed during glycine treatment was 3-fold greater than that observed during D-cycloserine treatment. The difference was highly significant (t=8.2, df=6, p<0.0001). These data provide the first direct comparison of effects of glycine and D-cycloserine in the same group of patients, and the first demonstration that the full agonist glycine is significantly more effective in the treatment of negative symptoms of schizophrenia than the partial agonist D-cycloserine. The finding that the full agonist, glycine, is superior to the partial agonist D-cycloserine suggests that other full agonists of the glycine site (or precursors thereof) should also be therapeutically beneficial in schizophrenia. Other potential agents to be used would include D-serine, D-alanine, glycineamide, threonine and poplypeptide precursors of such compounds.

TABLE 1

Demographic and treatment characteristics of study patients

| | | | Glycine study | | D-Cycloserine study | |
|---|---|---|---|---|---|---|
| Subject | Age | Gender | Medication | Dose (mg/day) | Medication | Dose (mg/day) |
| 1 | 57 | M | thioridazine | 250 | thioridazine | 100 |
| 2 | 44 | M | clozapine | 200 | clozapine | 200 |
| 3 | 24 | M | thioridazine | 50 | thioridazine | 100 |
| 4 | 49 | M | clozapine | 400 | clozapine | 400 |
| 5 | 25 | M | clozapine | 450 | risperidone | 6 |
| 6 | 63 | F | chlorpromazine | 300 | haloperidol | 40 |
| 7 | 30 | F | clozapine | 350 | clozapine | 400 |

Experiment #2 - Inhibition of PCP-induced hyperactivity by glycine-transport antagonists

RATIONALE

Earlier double blind, placebo-controlled trials of glycine in schizophrenia support the idea that NMDA augmenting agents will be beneficial in the treatment of schizophrenia. See U.S. Pat. No. 5,854,286. The clinical utility of this agent is limited, however, by the relatively large doses that are required to significantly elevate CNS glycine levels (Toth and Lajtha, 1986; D'Souza et al., 1995). The large doses are required because glycine permeates across the blood-brain barrier slowly by passive diffusion, and, once in the CNS, is sequestered intracellularly by glycine transporters. Two families of glycine transporters have been identified glycine type 2 (GLYT2) transporters are co-localized with inhibitory (strychnine-sensitive) glycine receptors in hindbrain and spinal cord and maintain low glycine levels within the synaptic cleft in those brain regions. In contrast, type 1 transporters (GLYT1) are co-localized with NMDA receptors in forebrain and hippocampus, and may serve to maintain low intrasynaptic glycine levels specifically in the local region around NMDA receptors. It is possible, therefore, that inhibition of GLYT1 transporters would lead to elevations of glycine levels in the immediate vicinity of NMDA receptors and augmentation of NMDA receptor-mediated neurotransmission without requiring administration of exogenous glycine. Support for such a hypothesis comes from a recent study in which co-expression of GLYT1 transporters along with NMDA receptors in Xenopus oocytes led to significant inhibition of NMDA receptor responsiveness (Supplison and Bergman, 1996). Blockade of GLYT1 transporters would thus theoretically be expected to exert an opposite effect. The use of glycine transport blockers to augment NMDA receptor-mediated neurotransmission would be analogous to the use of noradrenaline/serotonin reuptake inhibitors (rather than precursors such as tyrosine or tryptophan) to enhance monoaminergic neurotransmission.

In early preclinical studies investigating effects of glycine on PCP-induced hyperactivity, it was noted that a specific glycine derivative, GDA, was significantly more potent than glycine itself in reversing PCP-induced hyperactivity (Toth et al., 1986). Although the mechanism of action of GDA was unknown at the time of those initial studies, more recent research has demonstrated that GDA acts as a glycine transport inhibitor at doses similar to those used in behavioral studies (U.S. Pat. No. 5,837,730); Javitt and Frusciante, 1997; Javitt et al., 1997). To the extent that the behavioral effects of GDA are due to its inhibition of glycine transport, the ability of GDA to antagonize PCP-induced hyperactivity supports the concept that glycine transport inhibitors, particularly those acting at GLYT1 transporters, may be useful in the treatment of schizophrenia. However, because GDA may have idiosyncratic effects unrelated to its effects at the glycine transport site, it is important to test additional compounds with known affinity for glycine transporters. For this study, several novel GDA-related compounds were synthesized and their effects on PCP-induced hyperactivity and in vitro glycine transport were characterized. These compounds were structurally similar to GDA, but differed in the length of the carbon sidechain that was joined to the glycine backbone via the amide linkage. The length of carbon chain varied from 6 to 13 carbon atoms. The 6-carbon analog (G6A) was found in one early study not to significantly inhibit PCP-induced hyperactivity (Toth et al., 1986). The other agents (G8A, G10A, G11A and G13A) had not been synthesized previously.

Methods

Glycineamide derivatives were synthesized in house according to the approach of Toth et al (1986). The specific agents used for study were glycylhexylamide (G6A), glycyloctylamide (G8A), glycyldecylamide (G10A), glycylundecylamide (G11A) and glycyltriscadecylamide (G13A).

Behavioral studies were performed using BALB/c mice (25 g) of either sex. Rodent activity was monitored using a photocell-based activity meter (Columbus Instruments Auto-Track System, Columbus, Ohio). Animals were placed in test cages and allowed to accommodate overnight. On the day of experiment, animals, in their home cages, were placed on the activity monitors and baseline activity was monitored for 20 min., after which time animals were pretreated with either saline or a specified glycineamide derivative (0.1 g/kg i.p.). 30 min. after pretreatment, animals were injected with either PCP (5 mg/kg i.p.) or amphetamine (5 mg/kg s.c.). Activity was then monitored for an additional 90 minutes. For statistical analyses, summed activity over the 90 min. following PCP/amphetamine injection was used as a measure of drug-induced hyperactivity.

Synaptosomal $P_2$ fractions were prepared from cerebral cortex+hippocampus of Sprague-Dawley rats (200–250 g). Brain tissue was homogenized in 0.32 M sucrose in Tris-HCl buffer (pH 7.4), and centrifuged at 1,000×g for 10 min at 4° C. in a Sorvall 5C centrifuge. The supernatant was then centrifuged at 14,000×g for 10 min and the pellet resuspended in artificial CSF having the following composition (mM): NaCl, 125; KCl, 3; $MgSO_4$, 1.2; $CaCl_2$, 1.2; $NaH_2PO_4$, 1; $NaHCO_3$, 22; glucose, 10. Homogenate was aerated with 95% $O_2$/5% $CO_2$ until use. 1 ml aliquots of homogenate were preincubated with specific concentrations of glycineamide derivatives, following which incubation was initiated by the addition of 10 μl of 10 μM [$^3$H]glycine (DuPont/NEN or Sigma, spec. act.≈45 Ci/mmol) to obtain a final concentration of 100 nM. Nonspecific binding was determined in the presence of 10 mM sarcosine. Following 5 min, incubation was terminated by filtration under reduced pressure using a Brandel 24-well cell harvester and Whatman GF-B filters. Radioactivity was determined by scintillation counter with approximate efficiency of 50%.

Results

In prior studies, GDA has been found to inhibit PCP-induced hyperactivity at doses of 50–200 mg/kg i.p. For the present study, an initial experiment evaluated the specificity of the GDA effect. Rats were pre-treated with GDA (50 mg/kg i.p.) after which they received either PCP (5 mg/kg i.p.) or amphetamine (5 mg/kg i.p.). Both PCP and amphetamine induced significant levels of hyperactivity. Pretreatment with GDA did not significantly affect basal activity. However, GDA significantly reduced the degree of hyperactivity induced by PCP (t=4.09, p<0.001) (FIG. 2). In contrast, the level of hyperactivity induced by amphetamine was not significantly altered (t=0.59, p>0.5). GDA-induced inhibition of PCP-induced hyperactivity was significantly dose-dependent with 50 mg/kg GDA inducing a reduction of hyperactivity to below 70% of control (PCP alone) levels, and 100 mg/kg GDA inducing a reduction to below 50% of control (t=5.04, p<0.001) (FIG. 3).

Because it was assumed that the majority of glycineamide derivatives tested would be less potent that GDA in reversing PCP-induced hyperactivity, a dose of 100 mg/kg i.p. was chosen for comparative testing. As has been reported previously (Toth et al., 1986), glycylhexylamide (G6A) did not significantly inhibit PCP-induced hyperactivity. Significant reductions in activity were, however, observed following pretreatment with G10A, GDA,. and G13A, with the degree of reduction increasing with increasing length of the carbon sidechain (FIG. 3).

The potency with which the identified glycineamide derivatives inhibited glycine transport in vitro was analyzed using a synaptosomal assay system. All agents tested induced significant, dose-dependent inhibition of synaptosomal sarcosine-sensitive glycine uptake (FIG. 4). Agents with longer side chains showed greater potency for inhibition of glycine transport with IC50 values in the low micromolar range, whereas shorter chain derivatives showed IC50 values in the low to mid millimolar range. In order to compare the potency of these agents at a concentration relevant to the dose used for behavioral testing, all agents were re-tested for inhibitory potency at a single fixed concentration of 100 μg/ml. Significant variation was seen across compounds, with GDA, (t=18.6, p<0.0001), G13A (t=15.3, p<0.0001), G11A (tx6.79, p<0.001) and G10A (t=4.64, p<0.01) leading to significant inhibition of GLYT1-mediated transport, G8A having no significant effect (t=1.37, p>0.2), and G6A leading to significant potentiation of transport (t=4.2, p<0.1). The potency with which the glycineamide derivatives inhibited GLYT1-mediated synaptosomal glycine transport correlated significantly (p<0.05) with their potency in antagonizing PCP-induced hyperactivity (FIG. 5).

Other agents which should be useful for treating schizophrenia through inhibition of glycine transport include other glycylakylamides in which the alkyl group contains 3 to 30 carbon atoms, and structures containing branched, cyclic or polycyclic side chains.

REFERENCES

Davis K L, Kahn R S, Ko G, Davidson M (1991): Dopamine in schizophrenia: a review and reconceptualization. Am J Psychiatry 148:1474–1486.

Debler E A, Lajtha A (1987): High-affinity transport of n-aminobutyric acid, glycine, taurine, L-aspartic acid, and L-glutamatic acid in synaptosomal (P2) tissue: a kinetic and substrate specificity analysis. J Neurochem 48:1851–6.

D'Souza D C, Chamey D, Krystal J (1995): Glycine site agonists of the NMDA receptor: a review. CNS Drug Revs 1:227–260.

Hashimoto A, Oka T (1997): Free D-aspartate and D-serine in the mammalian brain and periphery. Prog. Neurobiol 52:325–353.

Heresco-Levy U, Javitt D C, Irmilov M, Mordel C, Horowitz A, Kelly D (1996): Double-blind, placebo-controlled, crossover trial of glycine adjuvant therapy for treatment-resistant schizophrenia. Br J Psychiatry 169:610–617.

Javitt D C, Sershen H, Hashim A, Lajtha A (1997): Reversal of phencyclidine-induced hyperactivity by glycine and the glycine uptake antagonist glycyldodecylamide. Neuropsychopharmacol 17:202–204.

Javitt D C, Frusciante M J. (1997): Glycyldodecylamide, a phencyclidine behavioral antagonist, blocks cortical glycine uptake: Implications for schizophrenia and substance abuse. Psychopharmacol. 129: 96–98.

Javitt D C, Zylberman I, Zukin S R, Heresco-Levy U, Lindenmayer J P (1994): Amelioration of negative symptoms in schizophrenia by glycine. Am J Psychiatry 151:1234–1236.

Javitt D C, Zukin S R (1991): Recent advances in the phencyclidine model of schizophrenia. Am J Psychiatry 148:1301–8.

Javitt D C, Zukin S R (1989): Interaction of[$^3$H]MK-801 with multiple states of the N-methyl-D-aspartate receptor complex of rat brain. Proc. Nat. Acad. Sci. USA 86:740–744.

Javitt D C (1987): Negative schizophrenic symptomatology and the phencyclidine (PCP) model of schizophrenia. Hill J Psychiat 9:12–35.

Kleckner N W, Dingledine R (1988): Requirement for glycine in the activation of NMDA-receptors expressed in Xenopus ooctyes. Science 241:835–837.

Leidernan E, Zylberman I, Javitt D C, Zukin S R, Cooper T B. Effect of high-dose oral glycine on serum levels and negative symptoms in schizophrenia. Biol. Psychiatry 1996;39:213–215.

Liu Q R, Lopez-Corcuera B, Mandiyan S, Nelson H, Nelson N (1993): Cloning and expression of spinal cord- and brain-specific glycine transporter with novel structural features. J Biol Chem 268:22802–8.

Matsui T, Sekiguchi M, Hashimoto A, Tomita V, Nishikawa T, Wada K (1995) Functional comparison of D-serine and glycine in rodents: the effect on cloned NMDA receptors and the extracellular concentration. J Neurochem. 65:454–458.

McBain C J, Kleckner N W, Wyrick S, Dingledine R (1989): Structural requirements for the glycine coagonist site of N-methyl-D-aspartate receptors expressed in Xenopus oocytes. Mol Pharmacol 36:556–565.

Reynold I J, Murphy S N, Miller R J (1987): 3H-labeled MK-801 binding to the excitatory amino acid receptor complex from rat brain is enhanced by glycine. Proc. Natl. Acad. Sci. USA 84:7744–7748.

Schell M J, Molliver M E, Snyder S H (1995). D-serine, an endogenous synaptic modulator: localization to astrocytes and glutamate-stimulated release. Proc. Natl. Acad. Sci. USA 92:3948–3952.

Smith K E, Borden L A, Hartig P R, Branchek T, Weinshank R L (1992): Cloning and expression of a glycine transporter reveal colocalization with NMDA receptors. Neuron 8:927–35.

Supplisson S, Bergman C (1997): Control of NMDA receptor activation by a glycine transporter co-expressed in Xenopus oocytes. J Neurosci 17:4580–90.

Tanii Y, Nishikawa T, Hashimoto A, Takahashi K (1991): Stereoselective inhibition by D- and L-alanine of phencyclidine-induced locomotor stimulation in the rat. Brain Res 563:281–284.

Tanii Y, Hishikawa T, Hashimoto A, Takahashi K (1994): Stereoselective antagonism by enantiomers of alanine an d-serine of phencyclidine-induced hyperactivity, stereotypy and ataxia. J. Pharmacol. Exp. Ther. 269:1040–1048.

Tsai G, Yang P, Chung L-C, Lange N, Coyle J T (1998): D-serine in the treatment of schizophrenia. Biol. Psychiatry 44:1081–1089.

Wood P L (1995): The co-agonist concept: is the NMDA-associated glycine receptor saturated in vivo? Life Sci 57:301–10.

Wong E H, Knight A R, Ransom R (1987) Glycine modulates [3H]MK-801 binding to the NMDA receptor in rat brain. Eur J Pharmacol 142:487–8.

Zafra F, Aragon C, Olivares L, Danbolt N C, Gimenez C, Storm-Mathisen J (1995): Glycine transporters are differentially expressed among CNS cells. J Neurosci 15:3952–69.

Variations of the invention will be apparent to the skilled artisan.

What is claimed:

1. A process for treating a human patient having a psychosis which comprises administering to said patient a full agonist substitute for glycine at the glycine-binding site of the NMDA receptor complex in an amount sufficient to potentiate NMDA receptor mediated neurotransmission.

2. The process of claim 1 wherein the psychosis is schizophrenia.

3. A process for treating a human patient having a psychosis which comprises administering to said patient threonine in an amount sufficient to potentiate NMDA receptor mediated neurotransmission.

4. The process of claim 3 wherein the psychosis is schizophrenia.

* * * * *